(12) United States Patent
Akiba

(10) Patent No.: US 7,371,211 B2
(45) Date of Patent: May 13, 2008

(54) BRANCHING PASSAGE ASSEMBLY FOR ENDOSCOPIC BIOPSY CHANNEL

(75) Inventor: Haruo Akiba, Saitama (JP)

(73) Assignee: Fujinon Corporation, Saitama (JP)

( * ) Notice: Subject to any disclaimer, the term of this patent is extended or adjusted under 35 U.S.C. 154(b) by 690 days.

(21) Appl. No.: 10/800,863

(22) Filed: Mar. 16, 2004

(65) Prior Publication Data

US 2004/0193183 A1 Sep. 30, 2004

(30) Foreign Application Priority Data

Mar. 28, 2003 (JP) .............................. 2003-091940

(51) Int. Cl.
*A61B 1/12* (2006.01)
(52) U.S. Cl. ...................... 600/156; 600/104; 600/153; 600/154; 600/157; 600/158; 600/159
(58) Field of Classification Search ......... 600/153–159
See application file for complete search history.

(56) References Cited

U.S. PATENT DOCUMENTS 5,735,793 A * 4/1998 Takahashi et al. .......... 600/153

\* cited by examiner

*Primary Examiner*—Linda C. M. Dvorak
*Assistant Examiner*—Matthew J. Kasztejna
(74) *Attorney, Agent, or Firm*—Oblon, Spivak, McClelland, Maier & Neustadt, P.C.

(57) ABSTRACT

Mounted internally of a casing of a manipulating head assembly of an endoscope is a branching passage member to connect a base end of a biopsy channel with a biopsy channel entrance way and a suction passage. The branching passage member is retained in position by threaded engagement with a biopsy channel entrance pipe which is fitted in the biopsy channel entrance way. Further, the branching passage member is provided with restrictive members thereby to restrict movements of the branching member except a movement toward the biopsy channel entrance pipe when the branching member is pulled into the biopsy channel entrance way for engagement with the entrance pipe.

14 Claims, 6 Drawing Sheets

BRANCHING PASSAGE ASSEMBLY FOR ENDOSCOPIC BIOPSY CHANNEL

BACKGROUND OF THE INVENTION

1. Field of the Art

This invention relates to medical endoscopes, and more particularly to a branching passage assembly for endoscopes which incorporate a forked branching member in a manipulating head assembly to connect a proximal end of a biopsy channel to a biopsy channel entrance passage and a suction passage.

2. Prior Art

Generally, medical endoscopes are largely constituted by a manipulating head assembly to be gripped and manipulated by an operator, an insertion tube extended out from one side of the manipulating head assembly for insertion into a body cavity, and a flexible light guide cable led out from the manipulating head assembly and provided with a connector at its proximal end which is disconnectibly connectible at least to a light source. Illumination and observation windows of optical image pickup means are provided on a rigid tip end section at the fore distal end of the insertion tube to carry out an endoscopic examination of an intracavitary site of interest under illuminated state.

It becomes possible to insert a biopsy or surgical instrument through an endoscope when a diseased portion or a bleeding site is spotted within a body cavity or when there arises a necessity for sampling tissues. For this purpose, in many cases a biopsy channel is provided in the endoscope and extend between a biopsy channel entrance way which is provided on the manipulating head assembly and an instrument outlet which is opened at the distal end of the insertion tube. The biopsy channel which is extended between the biopsy channel entrance way and the instrument outlet is usually constituted by a flexible tube. The biopsy channel of this sort is also utilized as a suction passage at the time of aspiration of body fluids or the like.

In order to comply with these requirements, a forked branching passage member is provided internally of the manipulating head assembly, thereby to connect a proximal end of a biopsy channel to either a biopsy channel entrance way or a suction passage. Accordingly, the forked branching passage member is internally provided with forked passages in communication with three connecting ends, i.e., a first connecting end to be connected with the biopsy channel, a second connecting end to be connected with the biopsy channel entrance way and a third connecting end to be connected with the suction passage.

Having the construction as described above, the branching passage member has to be retained in a fixed state within the manipulating head assembly of the endoscope. In this regard, it has been known in the art, for example, form Japanese Patent Publication No. 5-3287, to provide a tubular retainer member within a casing of the manipulating head assembly and to stop a branching passage member in the tubular retainer member by means of screws.

Taking into considerations the relations with a pipe of the biopsy channel entrance way and tubes of the biopsy channel and the suction passage, the branching passage member should be fixed in the first place in a position independently of and prior to connecting thereto the pipe and tubes just mentioned. That is to say, the pipe and tubes have to be connected to the branching passage member after fixation of the latter. The suction tube which has no possibilities of damages in use can be connected to the branching passage member securely by the use of an adhesive, and a connection can be made without any difficulty in particular. However, it may be made difficult to connect the pipe of the biopsy channel entrance way, a rigid pipe, to the branching passage member even by a positional deviation therebetween. Further, considering that the biopsy channel has possibilities of being damaged by insertion of a needle-like instrument in use, it should be disconnectibly connected to the branching passage member, and should be easily disconnectible when necessary. Nevertheless, once connected to the branching passage member, the biopsy channel tube should be retained stably in the connected state. Therefore, difficulties are often experienced in connecting the biopsy channel entrance pipe and then the biopsy channel after completely fixation of the branching passage member in the tubular retainer member.

SUMMARY OF THE INVENTION

With the foregoing situations in view, it is an object of the present invention to provide an endoscope of the type incorporating a forked branching passage member to connect a base end of a biopsy channel with a biopsy channel entrance pipe and a suction tube, with arrangements permitting to assemble or disassemble the branching passage member into and out of a casing of a manipulating head assembly of the endoscope in a facilitated manner and to retain the branching passage member in a stabilized state once assembled into the casing of the manipulating head assembly.

In accordance with the present invention, for achieving the above-stated objective, there is provided a branching passage assembly for an endoscope incorporating a forked branching member internally of a casing of a manipulating head assembly to connect a base end of a biopsy channel running through an insertion tube of the endoscope with a biopsy channel entrance way and a suction passage, characterized in that: the forked branching member is retained in position by threaded engagement with an inner end of a biopsy channel entrance pipe fitted in the biopsy channel entrance way; and the forked branching member is associated with restrictive members adapted to restrict movements of the branching member in all directions except a movement in a direction toward the biopsy channel entrance pipe when the branching member is pulled toward the latter for threaded engagement therewith.

In this instance, from the standpoint of electrical insulation and weight reduction, preferably a synthetic resin molding is used as the casing of the manipulating head assembly. The casing can be split into a main cover section and a grip cover section. A manipulating member of an angulation control mechanism is mounted on the main cover section, while an entrance way leading to a biopsy channel in the insertion tube of the endoscope is provided on the grip cover section to permit endoscopically introducing a biopsy or surgical instrument into a body cavity. From the side of the main cover section, a plural number of passage-forming structural members including at least first and second tubular members are successively provided within the casing. The first and second tubular members are connected with each other through a reinforcing ring, and the branching passage member is placed internally of the tubular members. In a preferred form of the invention, a notched void portion is provided in part of the first tubular member and the reinforcing ring which are fitted with each other, and laterally extending stopper blades are provided on the branching passage member to serve as restrictive members. The stopper blades are fitted in a notched portion of the reinforcing ring, in abutting engagement with vertical and horizontal surfaces at notched portions of the reinforcing ring. In this case, the second tubular member can be extended to enshroud the restrictive members of the branching passage member. Accordingly, in consideration of strength and machinability, it is preferred that the first and second tubular members as well as the reinforcing ring is made of a metal. Particularly, the reinforcing ring is preferred to be made of a metal of high strength such as stainless steel, while the first and second tubular members are preferred to be made of a lightweight metal such as aluminum or an aluminum alloy.

The branching passage member which serves to add a branch passage to a suction passage is formed in a forked shape having three connection ends, i.e., a first connecting portion to be joined with the biopsy channel tube, a second connecting portion to be joined with the suction tube, and a third connecting point to be joined with the biopsy channel entrance pipe. Of the three connecting portions, the third connecting portion to be connected to the biopsy channel entrance pipe is provided with an external screw on its outer periphery for threaded engagement with an internal screw which is provided on the side of the biopsy channel entrance pipe. For connection to the third connecting portion of the branching passage member, the biopsy channel entrance pipe is inserted in the biopsy channel entrance way on the grip cover section of the casing, and then a mouth piece with a detachable plug member is threaded into the biopsy channel entrance way. By so doing, the assembly of the biopsy channel entrance pipe and the branching passage member is automatically located in a predetermined position within the casing of the manipulating head assembly. Besides, within the passage-forming structural members which are provided in the casing of the manipulating head assembly, the restrictive members can be provided integrally with the branching passage member in such a way to restrict movements of the branching passage member in upward, downward and forward directions. In this case, the restrictive members are pressed against the passage-forming structural members upon threading the mouth piece into the biopsy channel entrance way. At this time, the biopsy channel entrance pipe is pushed in the inward direction and firmly connected with the branching passage member.

Since the biopsy channel tube is used for insertion of biopsy and surgical instruments, it can be damaged in use to necessitate repair or replacement. Therefore, it is desirable that the biopsy channel tube is easily detachable and removable from outside. For this purpose, an external screw is provided on the outer periphery of the first connecting portion of the branching passage member, on the rear side of a tapered fore end portion. After fitting a biopsy channel tube on the tapered fore end portion, a retaining nut is threaded onto the external screw of the first connecting portion. Whereupon, the biopsy channel tube is pressed and anchored on the tapered fore end portion of the first connecting portion. Holes are opened in a passage-forming structural member which circumvents the retaining nut, so that the retaining nut is accessible through one of the holes and can be unscrewed and removed from the external screw portion on the first connecting portion whenever necessary.

The above and other objects, features and advantages of the present invention will become apparent from the following description, taken in conjunction with the accompanying drawings which by way of example preferred embodiments of the invention. Needless to say, the present invention should not be construed as being limited to particular forms which are shown in the drawings for illustrative purposes.

DESCRIPTION OF PREFERRED EMBODIMENTS

Figure 1:
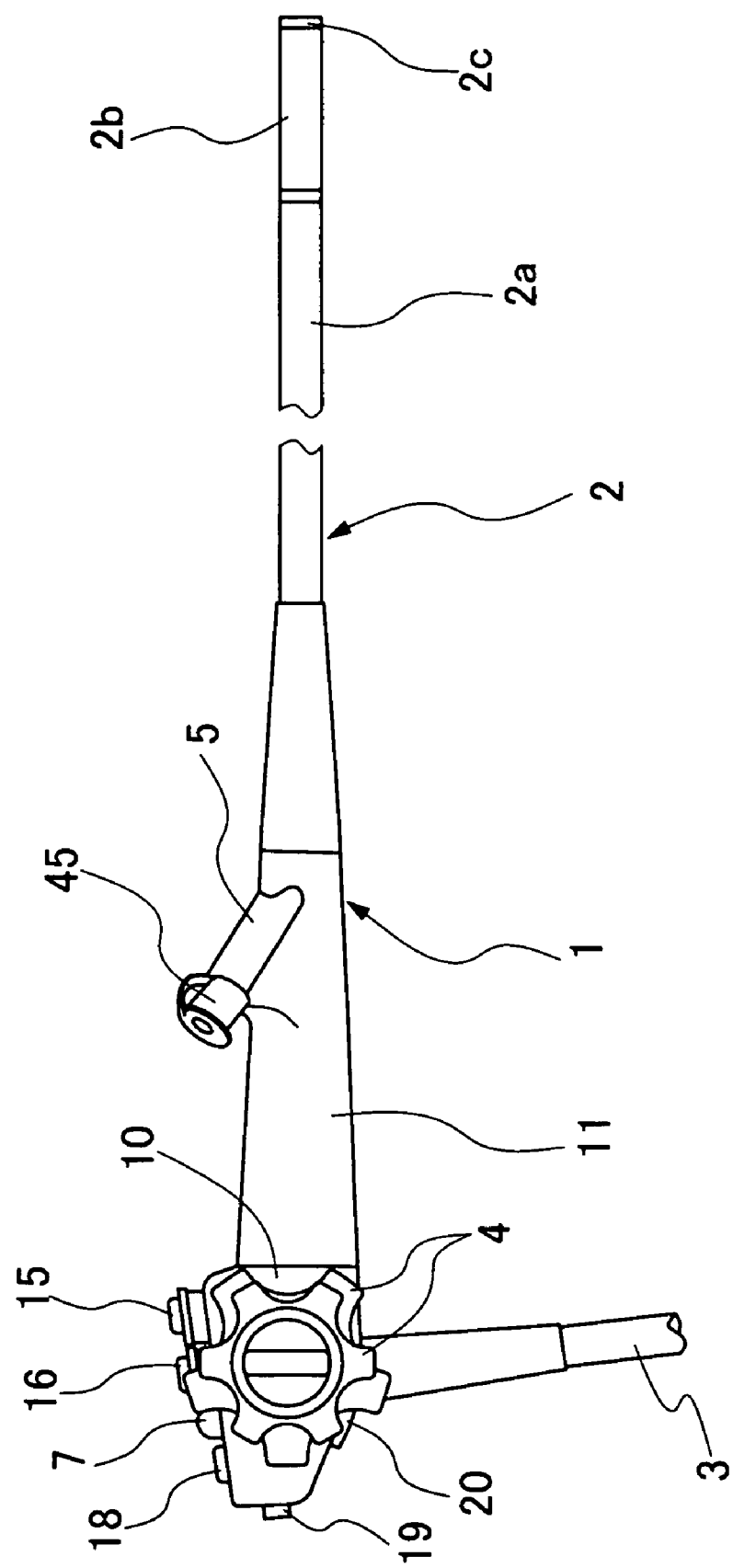
FIG. 1 is a schematic view showing general layout of an endoscope to which the present invention is applied.

Hereafter, the present invention is described more particularly by way of a preferred embodiment shown in the accompanying drawings. Referring first to FIG. 1, there is shown the general layout of an endoscope to which the present invention is applied. In that figure, indicated at 1 is a manipulating head assembly of the endoscope, at 2 an insertion tube and at 3 a flexible light guide cable. From a proximal end which is connected to the manipulating head assembly, a major part of the insertion tube 2 is constituted by an flexible body section 2a which is bendable in arbitrary directions within a body cavity. An angle section 2b and a rigid tip end section 2c are successively connected to the fore distal end of the flexible body section 2a. The angle section 2b can be bent arcuately by an angulating operation to turn the rigid tip end section 2c in a desired direction.

The angle section 2b is bent by remote control from side of the manipulating head assembly 1. For this purpose, an angulation knob 4 is provided on the manipulating head assembly 1 as a manipulating member of an angulation control mechanism. Further, in order to permit insertion of a biopsy or surgical instrument like forceps or a surgical high frequency instrument, an instrument outlet of a biopsy channel is opened on the rigid tip end section 2c of the insertion tube 2 in the vicinity of an endoscopic observation window, and an entrance way 5 to the biopsy channel is provided on the manipulating head assembly 1. As described in greater detail hereinafter, a flexible biopsy channel tube is connected between the biopsy channel entrance 5 and the instrument outlet to provide a biopsy channel internally of the insertion tube 2.

In use, the manipulating head assembly 1 is gripped in one hand of an operator for manipulation of the endoscope, at a position between the biopsy channel entrance way 5 and the angulation knob 4. Normally, the angulation knob 4 is arranged to be turned by a finger, particularly, by the thumb of the hand which grips the manipulating head assembly 1. By turning the angulation knob 4, angulation control wires are pulled forward and rearward to bend the angle section 2b to a desired degree in an aimed direction. When it becomes necessary to introduce a therapeutic instrument into a body cavity, the instrument can be inserted through the biopsy channel entrance way 5 by the other hand of the operator.

The manipulating head assembly 1 is housed in a casing of plastic molding, selected from the standpoint of electrical insulation and at the same time from the standpoint of weight reduction. The casing of the manipulating head assembly 1 is increased in thickness, that is to say, augmented in strength in a casing portion which supports the angulation knob 4, because large loads are imposed on that portion. On the other hand, in order to reduce the weight, the thickness of the casing is reduced in fore end portions forward of the angulation knob mount portion because no external forces are imposed there except the gripping force of an operator. Various component parts are accommodated within the manipulating head assembly 1. In order to assemble such internal component parts into the casing or in order to permit maintenance and service of internal component parts, the casing of the manipulating head assembly 1 is dividable into two parts. Namely, the casing of the manipulating head assembly 1 can be split into a main cover 10 with the angulation knob 4 and a grip cover 11 which extends between the main cover 10 and a fore distal end which is connected to the insertion tube 2. Accordingly, the main cover 10 is greater in wall thickness as compared with the grip cover 11. Further, from the standpoint of reducing the weight of the manipulating head assembly, the length of the main cover in the axial direction is made as short as possible, while accommodating in the thinner grip cover 11 the remaining lengthy part which is free of large external forces and loads.

Figure 2:
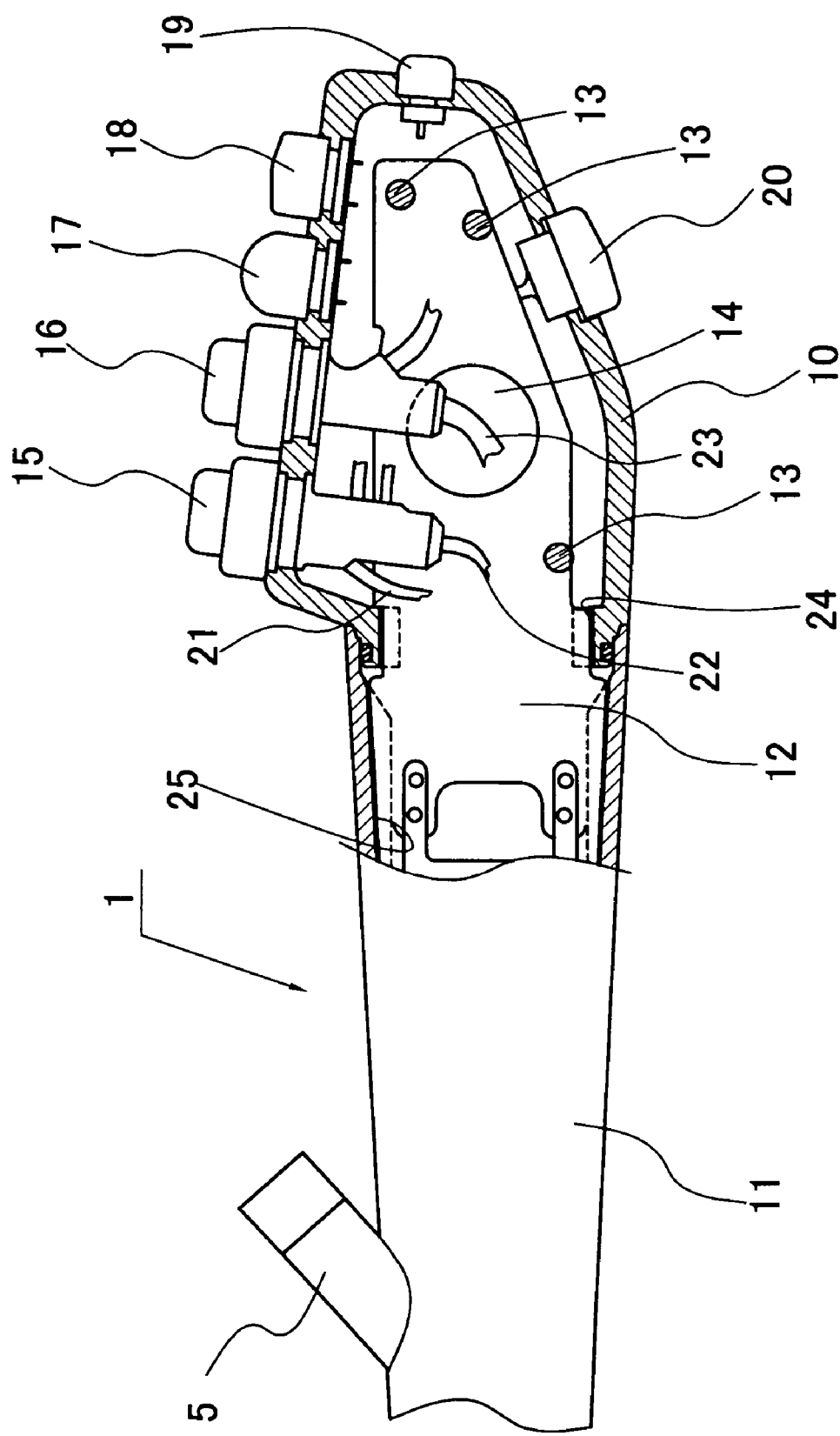
FIG. 2 is a schematic sectional view of a manipulating head assembly of the endoscope, showing internal construction under a main cover section of a casing of the manipulating head assembly.
Figure 3:
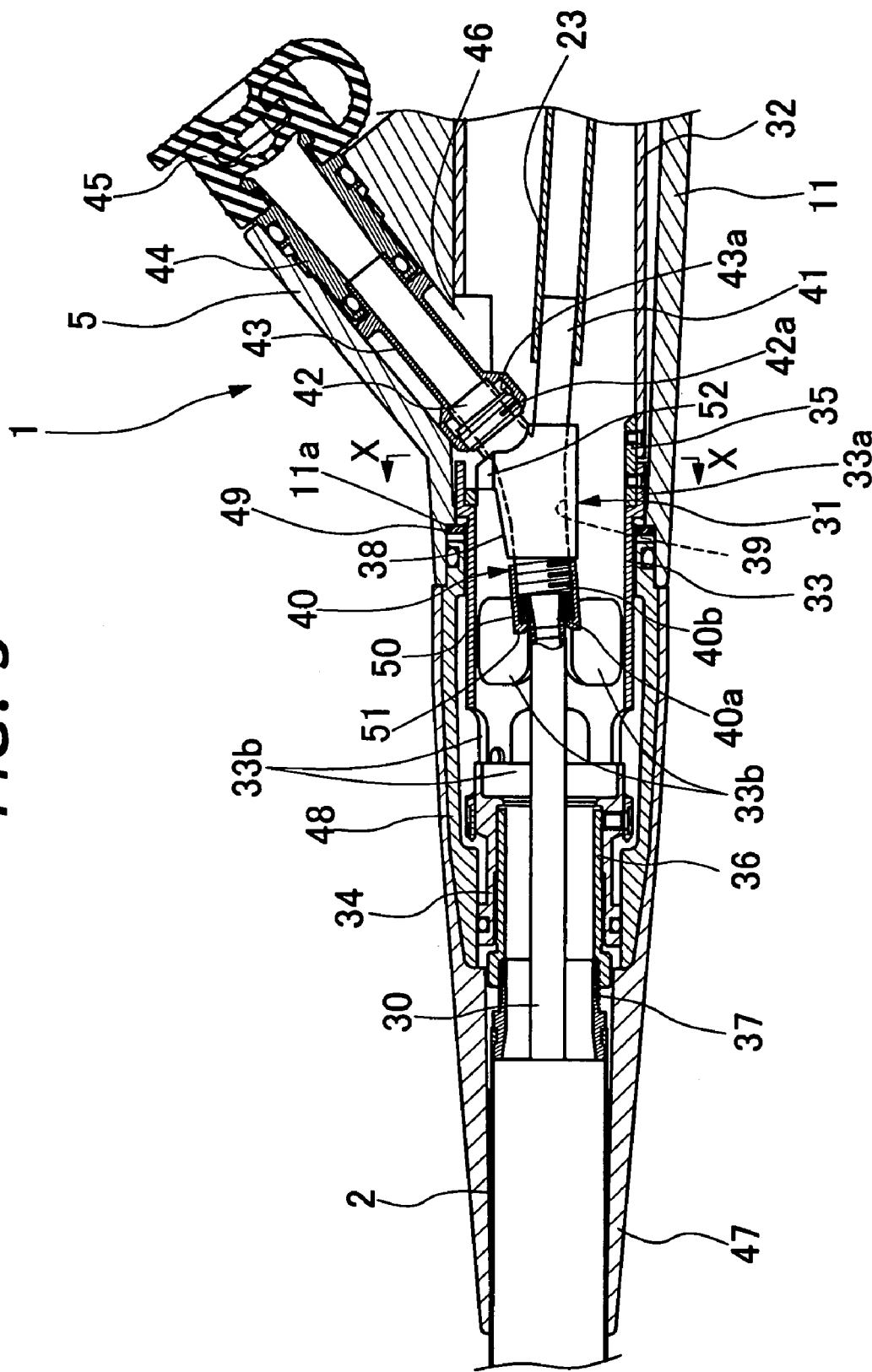
FIG. 3 is a schematic sectional view of the manipulating head assembly, showing internal construction under a grip cover section.

Now, turning to FIGS. 2 and 3, there are shown internal construction of the endoscope under the main cover 10 and internal construction under the grip cover 11, respectively.

As shown in FIG. 2, a support plate 12 is provided internally of the main cover 10. This support plate 12 is constituted by a rigid metal plate and securely fixed to a plural number of posts which are erected on the inner surface of the main cover 10. Mounted on the support plate 12 is an angulation pulley 14 which is turned by manipulation of the angulation knob 4. An air/water feed valve 15 and a suction valve 16 are provided on the main cover 10 along with various switches 17 to 20 for manipulation by an operator. An air feed tube 21 and a water feed tube 22 which are connected from the air/water feed valve 15 are extended into the insertion tube 2. Further, a suction tube 23 is connected to the suction valve 16. Opposite side edges of the support plate 12 are fitted in grooves 24 and 25 which are provided in joining end portions of the main cover 10 and the grip cover 11, more specifically, in fore end portions of the main cover 10 and in rear end portions of the grip cover 11, respectively. Thus, the main cover 10 and the grip cover 11 are fixed to each other in a locked state against relative movements in rotational directions.

As shown in FIG. 3, various component parts including light guides, signal cable, air feed tube 21, water feed tube 22, angulation control wires etc. are accommodated in the grip cover 11 and passed into the insertion tube 2. Further, a proximal end portion of a biopsy channel tube 30 is extended internally of the grip cover 11 for connection to the biopsy channel entrance way 5. Since the biopsy channel tube 30 is utilized also as a suction passage, a fore end portion of the suction tube 23 from the suction valve 16 also needs to be connected to the biopsy channel tube 30. In order to cope with this problem, a forked branching passage member 31 is located in a position in the proximity of the inner end of the biopsy channel entrance way 5 thereby to connect the biopsy channel tube 30 to both the biopsy channel entrance way 5 and the suction tube 23 through branch passages of the branching passage member 31.

A plural number of tubular passage-forming structural members are provided internally of the grip cover 11 for the purpose of positioning the branching passage member 31 and for passing the above-mentioned internal component parts. From the standpoint of shape retainability for the protection of the internally threaded component parts, the passage-forming structural members are desirably formed of a rigid metal. However, in order to reduce the weight as much as possible, a plural number of tubular members are connected one after another depending upon functions to be performed by the respective tubular members. More specifically, in the case of the particular embodiment shown, from the side of the rear end which is joined with the main cover 10, the passage-forming structural members are constituted by first to third tubular members 32 to 34. Rear end of the first tubular member 32 is securely connected to the support plate 12 by screws or other suitable fixation means, while its fore end is connected to the second tubular member 33 through a reinforcing ring 35. Fore end of the second tubular member 33 is fitted into the third tubular member 34 and connected to the latter by screws. Further, a connector ring 36 is threaded into the third tubular member 34, and fore end of the connector ring 36 is threaded onto an anchor ring 37 at the proximal base end of the insertion tube 2. For the sake of weight reduction, desirably thin tubes of an aluminum alloy or the like are employed as the first to third tubular members 32 to 34. The reinforcing ring 35 is arranged to have the smallest width for connecting the first and second tubular members 32 and 33, and made of stainless steel to ensure reliability in strength.

The branching passage member 31, which is located internally of the passage-forming structural members, is formed of strong material like metal, and provided with a forked passage 38 within its casing, having a first connecting portion 40 to be connected with the biopsy channel tube 30, a second connecting portion 41 to be connected with the suction tube 23, and a third connecting portion 42 to be connected with a biopsy channel entrance pipe 43 which is fitted in the biopsy channel entrance way 5. Outer end of the entrance pipe 43 is fitted in a mouth piece 44 which is projected from the outer end of the biopsy channel entrance way 5. A plug member 45 of resilient material is detachably fitted on the projected outer end of the mouth piece 44. Therefore, for connection with the entrance pipe 43, the third connecting portion 43 of the branching passage member 31 has to be projected toward the entrance pipe 43 through the passage-forming structural members. The point of projection of the branching passage member 31 is located at a joint portion of the first tubular member 32 and the reinforcing ring 35. Accordingly, a notched void portion 46 is provided at the joint portion of the reinforcing ring 35 and the first tubular member 32, and the third connecting portion 42 of the branching passage member 31 is projected outward through the notched void portion 46 and connected with the biopsy channel entrance pipe 43.

The fore end of the grip cover 11 is extended as far as a position which fully encloses the rear end of the second tubular member 33, and a rubber cover 47 is fitted continuously from the fore end of the grip cover 11. The rubber cover 47 is extended forward in such a manner as to cover, over a predetermined length, a rear or proximal end portion of the insertion tube 2 which is connected to the manipulating head assembly 1. A tubular shape retainer shell 48 is provided integrally on the inner side of the rubber cover 47 for the purpose of retaining the shape of the latter. The shape retainer shell 48 is fixed in position by threaded engagement with the second tubular member 33. An external screw is provided on outer peripheral surface of the second tubular member 33 for threaded engagement with a screw ring 49. The screw ring 49 is pressed against a stopper wall 11*a* which is formed at the fore end of the grip cover 11. Accordingly, a pressing force is constantly applied to the grip cover 11 in the direction of the main cover 10.

In this instance, a major part of the branching passage member 31 is located internally of the second tubular member 33, and its second connecting portion 41 is extended into the first tubular member 32. On the other hand, the third connecting portion 34 of the branching passage member 31 is projected in an obliquely upward direction through the notched void portion 46 and connected with the entrance pipe 43. Of the first to third connecting portions 40 to 42 of the branching passage member 31, the second connecting portion 43 is provided for connecting the biopsy channel with the section tube 23. Since there is no possibility of damages to the suction tube 23 when the endoscope is in use, it is strongly connected to the branching passage member 31 by the use of an adhesive or the like to prevent its separation under normal conditions.

In contrast, the biopsy channel tube 30 needs to be replaceably connected to the branching passage member 31 because damages and buckling might occur thereto, for example, as a result of insertion of a needle-like treating instrument. Therefore, the biopsy channel tube 30 is connected to the first connecting portion 40 of the branching passage member 31 in such a way as to permit its replacement. More particularly, for this purpose, the first connecting section 40 is provided with a tapered portion 40a where its outside diameter is gradually reduced in the forward direction, along with an external screw section 40b which is formed on the rear side of a maximum diameter portion of the tapered section 40a. On the other hand, a proximal end portion of the biopsy channel tube 30 is fitted on the first connecting portion 40 in such a manner as to ride over the tapered section 40 and anchored in position by the means of a taper ring 50, which is in turn stopped in position by threading a retaining nut 51 onto the external screw section 40b. Thus, the biopsy channel tub 30 is separably and fixedly connected with the first connecting portion 40 of the branching passage member 31.

The second connecting portion 42 of the branching passage member 31 is provided with an external screw section 42a on its outer periphery. The external screw 42a is threaded into an internal screw 43a which is formed on the inner periphery of a fore end portion of the biopsy channel entrance pipe 43, which is fitted in the biopsy channel entrance way 5.

Figure 4:
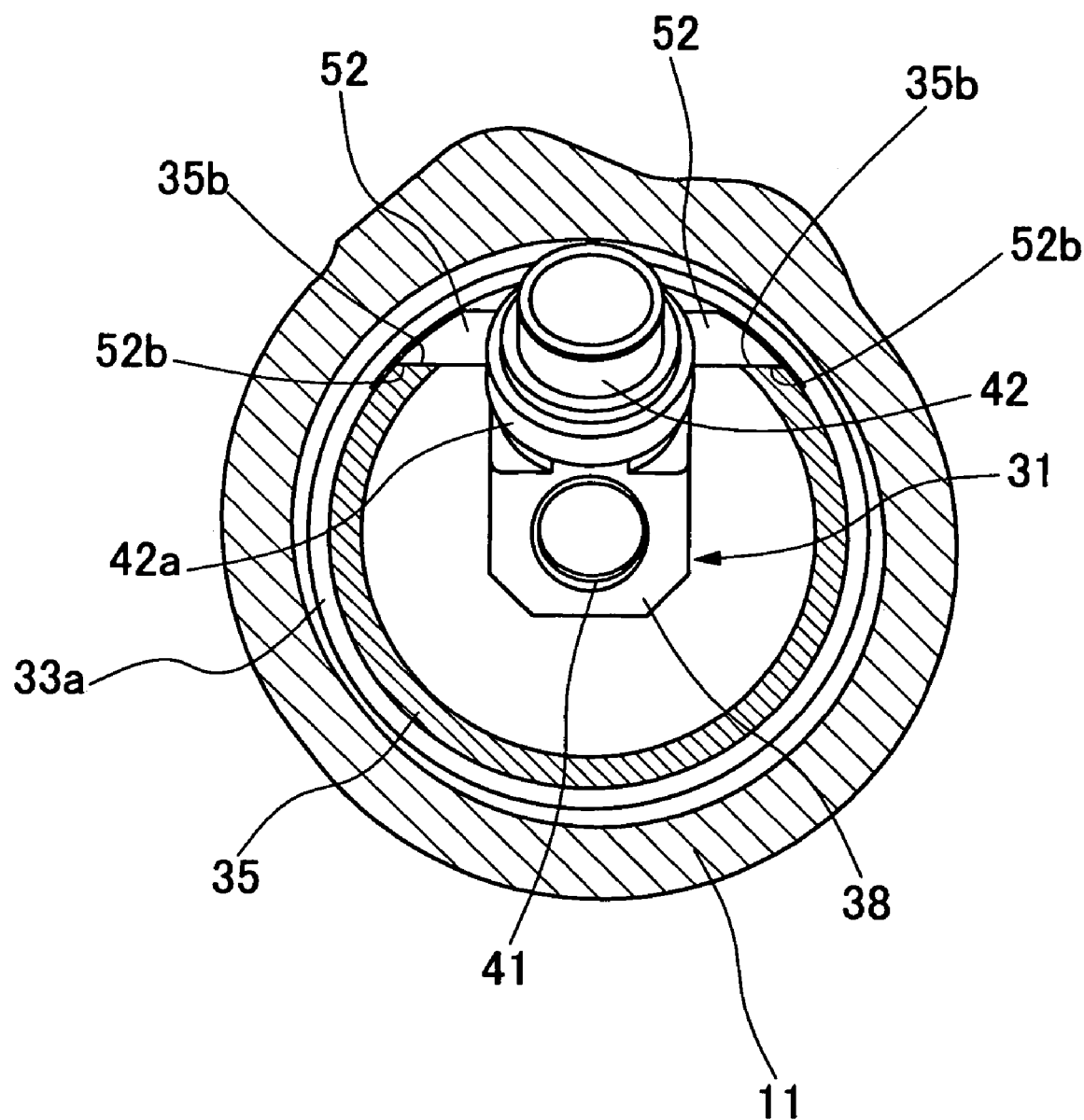
FIG. 4 is a schematic sectional view taken on line X-X in FIG. 3.
Figure 5:
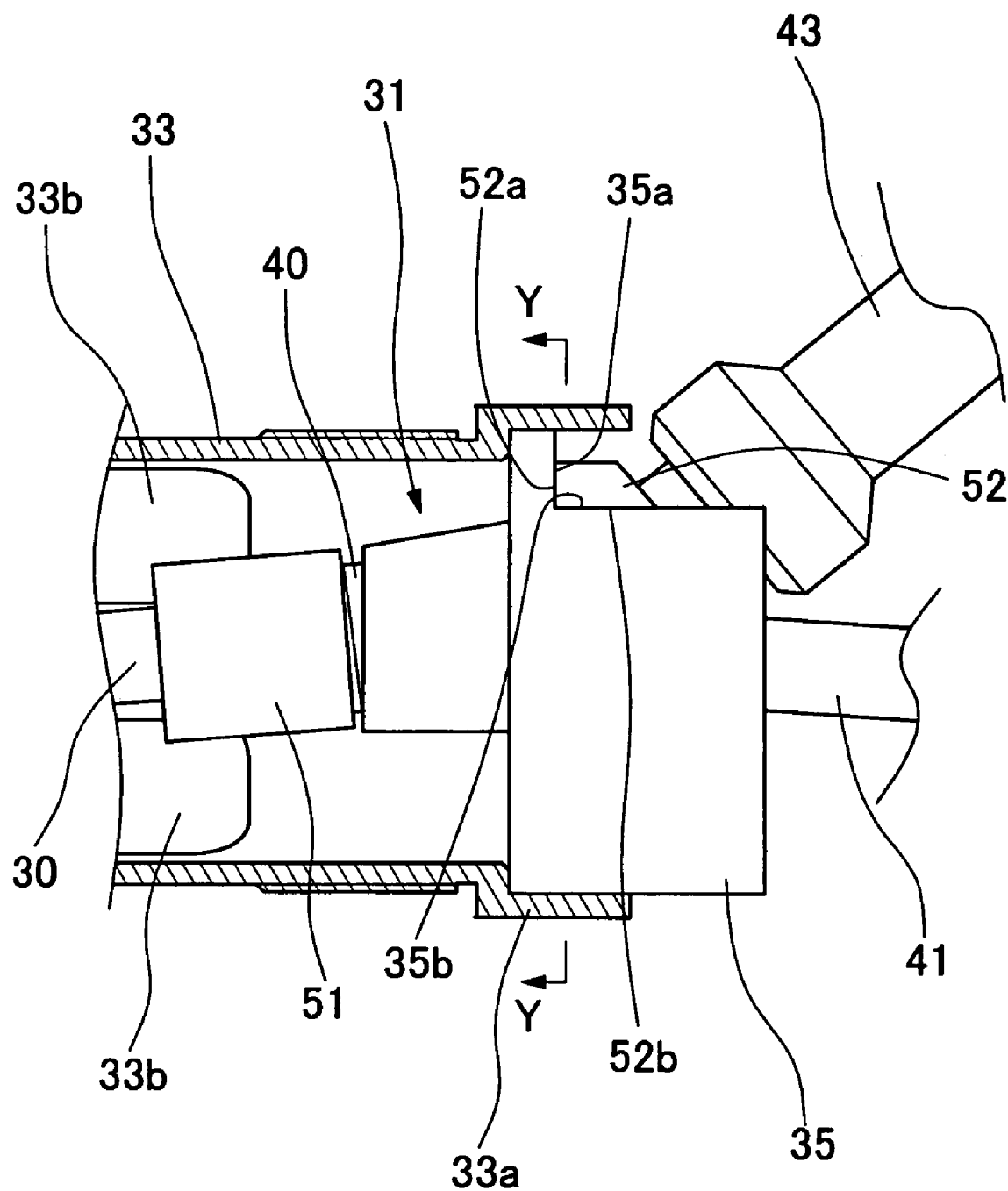
FIG. 5 is a schematic illustration showing a mount construction for a branching passage member.
Figure 6:
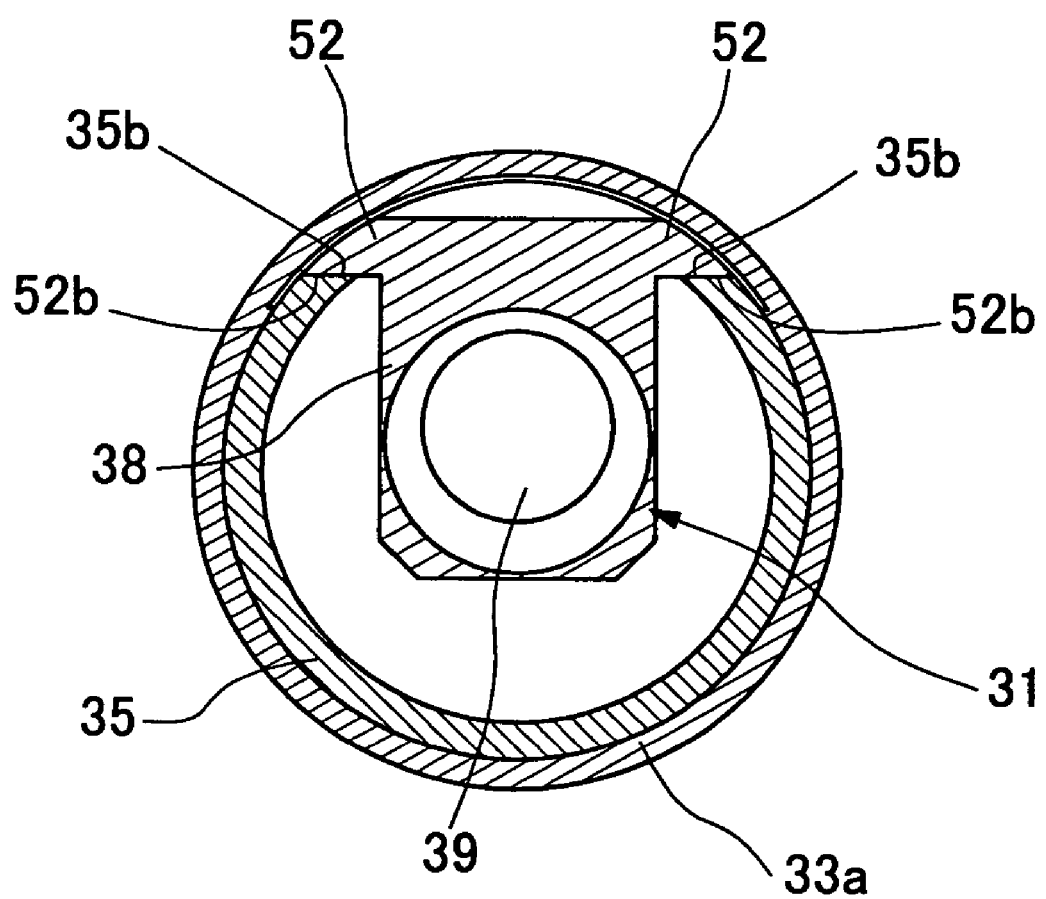
FIG. 6 is a schematic sectional view taken on line Y-Y in FIG. 5.

In this instance, the branching passage member 31 is not independently fixed in a certain position within the manipulating head assembly 1 but is arranged to be retained in a predetermined position when in an assembled state. For this purpose, as shown in FIGS. 4 to 6, the branching passage member 31 is provided with stopper blades 52 which are formed integrally with its casing 38 and projected in laterally opposite directions from an upper position of the casing 38. More specifically, these stopper blades 52 are formed on and integrally with the casing 38 at a position in the close proximity of the third connecting portion 42.

As described hereinbefore, the notched void portion 46 is formed in the first tubular member 32 and the reinforcing ring 35 for extending the third connecting portion 42 of the branching passage member 31 toward the biopsy channel entrance way 5. Vertical surfaces 52a at the projected outer ends of the stopper blades 52 are abutted against vertical surfaces 35a of the notched reinforcing ring 35, while lower surfaces 52b of the stopper blades 52 are abutted on horizontal surfaces 35b on the side of the reinforcing ring 35. Further, the second tubular member 33 is provided with a large diameter portion 33a at its base or proximal end. The outer diameter portion 33a of the second tubular member 33 is arranged to cover part of front side of the reinforcing ring 35 as well as upper portions of the stopper blades 52. As a consequence, the branching passage member 31 is restricted of forward movements by engagement of the vertical surfaces 52a of the stopper blades 52 with the vertical surfaces 35a of the reinforcing ring 35. Besides, movements in a downward direction are restricted by engagement of the lower surfaces 52b of the stopper blades 52 with the horizontal surfaces 35b of the reinforcing ring 35. It follows that dislodgement of the branching passage member 31 can be prevented by making the length of the stopper blades 52 between the projected ends of the lower surfaces 52b larger than the width between inner edges of the horizontal surfaces 35b of the reinforcing ring 35. Further, upward movements of the branching passage member 31 are restricted by the large diameter portion 33a of the second tubular member 33. Nevertheless, the branching passage member 31 is not completely fixed in these directions but is allowed to move to a certain degree in each direction.

In this stage, the third connecting portion 42 of the branching passage member 31 is not restricted of movements toward the biopsy channel entrance way 5. However, the third connecting portion 42 is connected with the biopsy channel entrance pipe 43, and the mouth piece 44 is threaded into the biopsy channel entrance way 5. Since the third connecting portion 42 is connected with the biopsy channel entrance pipe 43, the stopper blades 52 of the branching passage member 31 are pushed into corner portions between the vertical surfaces 35a and horizontal surfaces 35b of the reinforcing ring 35 through the biopsy channel entrance pipe 43 as soon as the mouth piece is threaded into the biopsy channel entrance way 5. At this time, the reinforcing ring 35 can be retained free of deformations or damages because it is formed of a metal of high strength like stainless steel as mentioned hereinbefore.

With the arrangements just described, in assembling the branching passage member 31 into the casing the manipulating head assembly 1 and connecting same with the biopsy channel tube 30, biopsy channel entrance pipe 43 and suction tube 23, the third connecting portion 42 of the branching passage member 31 can be automatically brought into an adjusted position relative to and in such a way as to follow up the biopsy channel entrance pipe 43 upon turning the biopsy channel entrance pipe 43 which is inserted in the biopsy channel entrance way 5. Accordingly, centering of the biopsy channel entrance pipe 43 and the third connecting portion 42 can be completed easily in a reliable manner. Being assembled in the manner as described above, thanks to the high strength of the reinforcing ring 35, the branching passage member 31 can be maintained in a stable state even if a large pressing force is exerted on the reinforcing ring 35 at the time of insertion of a biopsy or surgical instrument.

Thus, for assembling the branching passage member 31 into the casing of the manipulating head assembly 1, with the second tubular member 33 detached state from the reinforcing ring 35 which is connected to the first tubular member 32, the branching passage member 31 is inserted into the reinforcing ring 35 from the front side, letting the third connecting portion 42 project through the notched void portion 46 and placing the stopper blades 52 of the branching passage member 31 on the horizontal surfaces 35b of the reinforcing ring 35. Upon joining the second tubular member 33 with the reinforcing ring 35, the stopper blades 52 are restricted of movements in forward, upward and downward directions, and the third connecting portion 42 is projected toward the biopsy channel entrance way 5 is retained in that position.

Then, the biopsy channel entrance pipe 43 is inserted into the biopsy channel entrance way 5 through the outer open end and turned to thread its inner end onto the third connecting portion 42. As a result, the third connecting portion 42 is joined with the biopsy channel entrance pipe 43. In this instance, even if a relative positional deviation exists between the third connecting portion 42 of the branching passage member 31 and the biopsy channel entrance pipe 43, they are centered relative to each other by movements of the third connecting portion 42 and accurately joined with each other in a smooth and quick manner. Further, the mouth piece 44 is inserted and threaded into the biopsy channel 5 to fit a fore or inner end portion of the mouth piece 44 on the biopsy channel entrance pipe 43, pushing the biopsy channel entrance pipe 43 inward of the manipulating head assembly 1. As a result, the stopper blades 52 of the branching passage member 31 are pressed against the vertical surfaces 35a and horizontal surfaces 35b of the notched reinforcing ring 35 of high strength. Thus, the branching passage member 31 is retained in position in a stabilized state and restrained of spontaneous movements when in use.

When the manipulating head assembly 1 is in an assembled state, the branching passage member 31 can be dismantled after disconnecting the biopsy channel tube 30 from the branching passage member 31. More specifically, for this purpose, the mouth piece 44 is removed from the biopsy channel entrance way 5, and then the biopsy channel entrance pipe 43 is disconnected from the branching passage member. In this state, the branching passage member 31 is displaced toward the rear side by sliding the stopper blades 52 of the branching passage member 31 in the rearward direction toward the first tubular member 32, bringing the branching passage member 31 to an open position under the notched void portion 46 from the position which is enclosed by the second tubular member 33. The branching passage member 31, which is now freed from restrictions, can be taken out through the notched void portion 46.

Within the manipulating head assembly 1 with the branching passage member 31, the first tubular member 32 is connected to the support plate 12, and the third tubular member 34 is connected to the insertion tube 2 through the connector ring 36. Therefore, it is necessary for the first and third tubular members 32 and 34 to have a certain degree of strength. On the other hand, the second tubular member 33 which is reduced in thickness and formed with lightening holes 33b should be formed of a material of higher strength, for example, a material such as super-duralumin having hard alumite or anodized aluminum surfaces. The lightening hole 33b in the second tubular member 33 is provided at two spaced positions in the axial direction and at four spaced positions in the radial directions, namely, the lightening holes 33b are provided at eight different positions in total. The four lightening holes 33b in the rear side are formed in radially staggered positions relative to the four lightening holes 33b in the front side of the second tubular member 33, or vice versa. Besides, the lightening holes 33b are enshrouded by the shape retainer shell 48 which is integrally provided on the inner side of the rubber cover 47.

Therefore, after removing the shape retainer shell 48 which is integrally assembled with the rubber cover 47, a screw turning jig is inserted into the second tubular member 33 through a lightening hole 33b to unscrew and remove the retaining nut 51 of the biopsy channel tube 30. As a consequence, it becomes possible to remove or replace the biopsy channel tube 30. In this manner, the biopsy channel tube 30 can be connected or disconnected to and from the branching passage member 31 without disassembling built-in internal component parts on the rear side of the second tubular member 33. This means that repair jobs on the branching passage member as well as replacements of the biopsy channel 30 can be carried out in a facilitated manner.

What is claimed is:

1. A branching passage assembly for an endoscope comprising:

a forked branching member internally positioned in a casing of a manipulating head assembly to connect a base end of a biopsy channel running through an insertion tube of said endoscope with a biopsy channel entrance way and a suction passage, wherein said forked branching member is retained in position by threaded engagement with an inner end of a biopsy channel entrance pipe fitted in said biopsy channel entrance way, and said forked branching member is associated with restrictive members arranged to restrict movements of said branching member in all directions except a movement in a direction toward said biopsy channel entrance pipe when said branching member is pulled toward the latter for threaded engagement therewith, said casing of said manipulating head assembly is formed by joining a main cover section and a grip cover section, and arranged to support a manipulating member of an angulation control mechanism on said main cover section and to accommodate said branching member internally of said grip cover section, said branching member is located internally in passage-forming structural members including first and second tubular members provided internally in said casing of said manipulating head assembly to extend from said main cover section to said grip cover section and connected with each other through a reinforcing ring, and a notched void portion is provided in part of said first tubular member and said reinforcing ring, said second tubular member being fitted on said reinforcing ring, said forked branching member having a threaded connecting portion projected toward said biopsy channel entrance pipe through said notched void portion, said restrictive members being constituted by a pair of laterally projecting stopper blades provided on said branching member, said stopper blades being placed in said notched void portion and held in abutting engagement with vertical and horizontal surfaces at notched portions of said reinforcing ring within said second tubular member.

2. A branching passage assembly as defined in claim 1, wherein said first and second tubular members comprise a lightweight metal, and said reinforcing ring is a high strength metal ring.

3. A branching passage assembly as defined in claim 1, wherein said forked branching member is configured to be connected to a first connecting portion for connection of a biopsy channel tube, a second connecting portion for connection of a suction tube, and a third connecting portion for connection of a biopsy channel entrance pipe.

4. A branching passage assembly as defined in claim 3, wherein said third connecting portion is provided with an external screw on an outer peripheral surface while said biopsy channel entrance pipe is provided with an internal screw to be brought into threaded engagement with said external screw of said third connecting portion.

5. A branching passage assembly as defined in claim 4, wherein said biopsy channel entrance pipe is placed in said biopsy channel entrance way on said manipulating head assembly and threaded onto said third connecting portion, and a mouth piece with a plug member is threaded into said biopsy channel entrance way with a fore end portion thereof in fitting engagement with a rear or outer end portion of said biopsy channel entrance pipe.

6. A branching passage assembly as defined in claim 5, wherein passage-forming structural members are fitted in said casing of said manipulating head assembly, and said restrictive members are constituted by stopper portions formed integrally with said branching member and adapted to restrict movements of said branching member in upward, downward and forward directions, and said mouth piece is fitted on said biopsy channel entrance pipe in such a way as to press said restrictive members against a passage-forming structural member.

7. A branching passage assembly as defined in claim 6, wherein said first connecting portion is formed with an external screw portion on outer periphery thereof on the rear side of a tapered fore end portion, said biopsy channel tube being fitted on said tapered fore end portion of said first connecting portion and anchored in position by a retaining nut threaded onto said external screw portion, and said passage-forming structural member being provided with holes at positions around said retaining nut thereby permitting to separate said retaining nut from said external screw portion from outside of said passage-forming structural member.

8. A branching passage assembly for an endoscope comprising:
a manipulating head assembly having a casing;
a forked branching member internally positioned in the casing of the manipulating head assembly and configured to connect a base end of a biopsy channel running through an insertion tube of the endoscope with a biopsy channel entrance way and a suction passage, the forked branching member being retained in position by threaded engagement with an inner end of a biopsy channel entrance pipe fitted in the biopsy channel entrance way; and
restrictive means for restricting movements of the branching member in all directions except a movement in a direction toward the biopsy channel entrance pipe when the branching member is pulled toward the biopsy channel entrance pipe for threaded engagement therewith,
wherein the casing of the manipulating head assembly is formed by joining a main cover section and a grip cover section, and arranged to support a manipulating member of an angulation control mechanism on the main cover section and to accommodate the branching member internally in the grip cover section, the branching member is located internally in passage-forming structural members including first and second tubular members provided internally in the casing of the manipulating head assembly to extend from the main cover section to the grip cover section and connected with each other through a reinforcing ring, and a notched void portion is provided in part of the first tubular member and the reinforcing ring, the second tubular member being fitted on the reinforcing ring, the forked branching member having a threaded connecting portion projected toward the biopsy channel entrance pipe through the notched void portion, the restrictive means comprising a pair of laterally projecting stopper blades provided on the branching member, the stopper blades being placed in the notched void portion and held in abutting engagement with vertical and horizontal surfaces at notched portions of the reinforcing ring within the second tubular member.

9. A branching passage assembly as defined in claim 8, wherein the first and second tubular members comprise a lightweight metal, and the reinforcing ring comprises a high strength metal ring.

10. A branching passage assembly as defined in claim 8, wherein the forked branching member is configured to be connected to a first connecting portion of a biopsy channel tube, a second connecting portion of a suction tube, and a third connecting portion of a biopsy channel entrance pipe.

11. A branching passage assembly as defined in claim 10, wherein the third connecting portion has an external screw on an outer peripheral surface while the biopsy channel entrance pipe has an internal screw to be brought into threaded engagement with the external screw of the third connecting portion.

12. A branching passage assembly as defined in claim 11, wherein the biopsy channel entrance pipe is placed in the biopsy channel entrance way on the manipulating head assembly and threaded onto the third connecting portion, and a mouth piece with a plug member is threaded into the biopsy channel entrance way with a fore end portion thereof in fitting engagement with a rear or outer end portion of the biopsy channel entrance pipe.

13. A branching passage assembly as defined in claim 12, further comprising passage-forming structural members fitted in the casing of the manipulating head assembly, wherein the restrictive means comprises stopper portions formed integrally with the branching member and configured to restrict movements of the branching member in upward, downward and forward directions, and the mouth piece is fitted on the biopsy channel entrance pipe in such a way as to press the restrictive members against a passage-forming structural member.

14. A branching passage assembly as defined in claim 13, wherein the first connecting portion has an external screw portion on outer periphery thereof on the rear side of a tapered fore end portion, the biopsy channel tube being fitted on the tapered fore end portion of the first connecting portion and anchored in position by a retaining nut threaded onto the external screw portion, and the passage-forming structural member being provided with holes at positions around the retaining nut thereby permitting to separate the retaining nut from the external screw portion from outside of the passage-forming structural member.

* * * * *